(12) United States Patent
Kelvered et al.

(10) Patent No.: US 9,327,098 B2
(45) Date of Patent: May 3, 2016

(54) FIXATION DEVICE (75) Inventors: Jenny Kelvered, Alingsäs (SE); Tomas Fabo, Mölnlycke (SE)

(73) Assignee: Mölnlycke Health Care AB, Göteborg (SE)

( * ) Notice: Subject to any disclaimer, the term of this patent is extended or adjusted under 35 U.S.C. 154(b) by 393 days.

(21) Appl. No.: 13/820,780

(22) PCT Filed: Sep. 7, 2011

(86) PCT No.: PCT/SE2011/051083
§ 371 (c)(1),
(2), (4) Date: Mar. 5, 2013

(87) PCT Pub. No.: WO2012/033456
PCT Pub. Date: Mar. 15, 2012

(65) Prior Publication Data
US 2013/0165865 A1    Jun. 27, 2013

Related U.S. Application Data

(60) Provisional application No. 61/381,449, filed on Sep. 10, 2010.

(30) Foreign Application Priority Data

Sep. 10, 2010  (SE) .................................... 1050938-8

(51) Int. Cl.
*A61M 25/02*    (2006.01)
*A61M 5/158*    (2006.01)
*A61F 13/00*    (2006.01)

(52) U.S. Cl.
CPC .............. *A61M 25/02* (2013.01); *A61M 5/158* (2013.01); *A61F 2013/00417* (2013.01); *A61M 2025/0266* (2013.01); *A61M 2025/0273* (2013.01)

(58) Field of Classification Search
CPC ..................... A61M 25/02; A61M 2025/0266; A61M 2025/0273; A61F 2013/00417; A61F 2013/00421
See application file for complete search history.

(56) References Cited

U.S. PATENT DOCUMENTS

| 1,491,011 A | 4/1924 | Hodgin ........................ 128/850 |
| 3,630,195 A | 12/1971 | Santomieri ................... 128/133 |

(Continued)

FOREIGN PATENT DOCUMENTS

| CN | 200994982 | 12/2007 |
| EP | 0076896 | 4/1983 |

(Continued)

OTHER PUBLICATIONS

International Search Report issued on Dec. 15, 2011 for International Patent Application No. PCT/SE2011/051083, which was filed on Sep. 7, 2011 [Inventor—Kelvered; Applicant—Mölnlycke Health Care AB] [7 pages].

(Continued)

*Primary Examiner* — Bradley Osinski
(74) *Attorney, Agent, or Firm* — Ballard Spahr LLP (57) ABSTRACT

Provided is a fixation device for retaining a skin penetrating medical device, such as a cannula, on the skin of a patient. The fixation device includes a retaining component including a support layer having an adhesive coating, and a landing zone component, including a support layer having an adhesive coating, the landing zone component being adapted to be adhesively attached to the skin around the point of penetration. The retaining component acts as a skin-contacting component and is adapted to be applied on top of the landing zone component, and at least partially cover the medical device, such that the adhesive coating of the retaining component is applied to the support layer of the landing zone component. The adhesive coating of the retaining component includes a first adhesive, and the adhesive coating of the landing zone component includes a second adhesive, the first adhesive being different from the second adhesive.

22 Claims, 4 Drawing Sheets

(56) References Cited

U.S. PATENT DOCUMENTS

| | | | |
|---|---|---|---|
| 3,834,380 A | 9/1974 | Boyd | |
| 3,918,446 A | 11/1975 | Buttaravoli | 128/133 |
| 3,973,565 A * | 8/1976 | Steer | 604/180 |
| 4,275,721 A | 6/1981 | Olson | 128/133 |
| 4,336,806 A | 6/1982 | Eldridge | 128/348 |
| 4,485,809 A | 12/1984 | Dellas | 128/156 |
| 4,621,029 A | 11/1986 | Kawaguchi | 428/447 |
| 4,753,232 A | 6/1988 | Ward | 128/156 |
| 4,822,342 A | 4/1989 | Brawner | 604/180 |
| 4,867,748 A | 9/1989 | Samuelsen | |
| 4,898,587 A * | 2/1990 | Mera | 604/174 |
| 4,941,882 A | 7/1990 | Ward | 604/180 |
| 5,153,040 A | 10/1992 | Faasse | 428/40 |
| 5,356,428 A | 10/1994 | Way | |
| 5,490,504 A | 2/1996 | Vrona | |
| 5,540,922 A * | 7/1996 | Fabo | 424/402 |
| 5,566,031 A | 10/1996 | Meyr | 359/883 |
| 5,578,013 A | 11/1996 | Bierman | |
| 5,635,201 A | 6/1997 | Fabo | 424/443 |
| 5,722,965 A | 3/1998 | Kuczynski | |
| 5,755,681 A | 5/1998 | Plews | |
| 5,810,781 A | 9/1998 | Bierman | |
| 5,891,076 A | 4/1999 | Fabo | 602/52 |
| 5,944,696 A | 8/1999 | Bayless | 604/174 |
| 5,968,000 A * | 10/1999 | Harrison et al. | 602/41 |
| 6,015,119 A | 1/2000 | Starchevich | |
| 6,117,111 A | 9/2000 | Fleischmann | 604/180 |
| 6,124,521 A * | 9/2000 | Roberts | 602/54 |
| 6,132,399 A | 10/2000 | Shultz | 604/174 |
| 6,293,281 B1 | 9/2001 | Shultz | 128/888 |
| 6,436,073 B1 | 8/2002 | Von Teichert | 604/174 |
| 6,479,724 B1 | 11/2002 | Areskoug et al. | |
| 6,607,995 B1 | 8/2003 | Takeuchi | 442/327 |
| 6,866,949 B2 | 3/2005 | Ota et al. | |
| 7,506,647 B2 | 3/2009 | Worthington | |
| 8,652,112 B2 | 2/2014 | Johannison | |
| 2002/0026152 A1 * | 2/2002 | Bierman | 604/174 |
| 2004/0102744 A1 | 5/2004 | Fattman | 604/344 |
| 2005/0205099 A1 | 9/2005 | Gellerstedt et al. | |
| 2007/0073211 A1 | 3/2007 | Propp | 602/57 |
| 2007/0079831 A1 | 4/2007 | Worthington | |
| 2008/0045905 A1 | 2/2008 | Chawki | 604/263 |
| 2008/0114278 A1 | 5/2008 | Fabo | 602/48 |
| 2010/0307513 A1 | 12/2010 | Svensby | 602/54 |
| 2013/0281906 A1 | 10/2013 | Fabo | |

FOREIGN PATENT DOCUMENTS

| | | |
|---|---|---|
| EP | 0300620 | 1/1989 |
| EP | 1424088 | 6/2004 |
| GB | 1280631 | 7/1972 |
| JP | 2710431 | 2/1998 |
| SE | 510907 | 7/1999 |
| WO | WO-8911262 | 11/1989 |
| WO | WO 98/15312 | 4/1998 |
| WO | WO 99/61077 | 12/1999 |
| WO | WO 02/083206 | 10/2002 |
| WO | WO 03/079919 | 10/2003 |
| WO | WO 2006/075950 | 7/2006 |
| WO | WO-2006075948 | 7/2006 |
| WO | WO 2009/031948 | 3/2009 |
| WO | WO 2009/075636 | 6/2009 |

OTHER PUBLICATIONS

International Preliminary Report on Patentability issued on Mar. 12, 2013 and Written Opinion issued on Dec. 15, 2012 for International Patent Application No. PCT/SE2011/051083, which was filed on Sep. 7, 2011 [Inventor—Kelvered; Applicant—Mölnlycke Health Care AB] [13 pages].

* cited by examiner

FIXATION DEVICE

CROSS-REFERENCE TO RELATED APPLICATIONS

The present application is a U.S. National Phase Application of International Application No. PCT/SE2011/051083, filed Sep. 7, 2011, which claims priority to Swedish Patent Application No. 10509384, filed Sep. 10, 2010, and U.S. Patent Application No. 61/381,449, filed Sep. 10, 2010, all of which applications are incorporated herein fully by this reference.

TECHNICAL FIELD

The present invention relates to a fixation device for retaining a skin penetrating medical device, such as a cannula, on the skin of a patient, to a landing zone component, a method of affixing a skin penetrating medical device to the skin of a patient, and the use of a plastic film as a landing zone component.

BACKGROUND

When applying an IV medical device, such as a cannula, to a patient, the medical device needs to be retained to the skin of the patient. This is typically done by means of an adhesive dressing, such as an adhesive tape or adhesive patch. In order to hold the medical device securely to the skin, the adhesive dressing needs to exert a relatively strong adhesive force on the skin. Acrylic adhesives are often used for this purpose. An example of an adhesive dressing for retaining a cannula on the skin is disclosed in U.S. Pat. No. 4,941,882.

When cannula fixation dressings hitherto available are to be attached to a patient, the medical staff often need to use both hands when removing the dressing from its package or removing any release sheet from the adhesive coating, and applying the dressing to the patient, while they also at the same time need to hold the cannula after having punctured the patient, to prevent the cannula from falling off, or end up in an undesirable position. Applying a cannula to a patient therefore often involves two nurses, in particular when the patient is very movable.

A medical device, such as a cannula, which is fixated to the skin for some time is likely to cause imprints on the skin. This may cause irritation of the skin and be hurtful for the patient.

It is important that the medical device is held safely to the skin, and therefore there is a risk that the adhesive commonly used in the known dressings may harm the skin of the patient, especially patients with fragile or sensitive skin, or patients who need to have this kind of medical device applied for a long time.

There is thus a need for an improved fixation device for retaining a skin penetrating medical device to the skin, which is user-friendly and easy to apply.

SUMMARY OF THE INVENTION

The present invention provides an improved fixation device for retaining a skin penetrating medical device, such as a cannula, on the skin of a patient, which includes a landing zone component, to be applied directly to the skin of a patient, and a retaining component, to be applied on top of the landing zone component and is designed to retain the medical device on the surface of the landing zone component.

The landing zone component acts as a skin-contacting component, and includes a support layer having an adhesive coating, and is adapted to be adhesively attached to the skin around the point of penetration. The retaining component is designed to securely affix a medical device, and includes a support layer having an adhesive coating, and is adapted to be applied on top of the landing zone component, and to at least partially cover the skin penetrating medical device, such that the adhesive coating of the retaining component is applied to the support layer of the landing zone component. The skin of the patient can thus be protected from imprints from the medical device and skin irritation that may be caused by the medical device scraping the skin can be avoided. The adhesive coating of the retaining component comprises a first adhesive, and the adhesive coating of the landing zone component comprises a second adhesive, said first adhesive being different from said second adhesive, thus providing a more flexible and reliable fixation device, since the landing zone component may be designed to have adhesive properties which are different from the adhesive properties of the retaining component.

The invention also relates to a landing zone component for use in a fixation device for retaining a skin penetrating medical device as describe above, wherein the landing zone component comprises a support layer having an adhesive coating, and is provided with an opening, through which a skin penetrating medical device can pass when the landing zone component is applied to the skin of a patient, thereby achieving protection of the skin and easy application of the landing zone.

Further, the invention relates to a method of affixing a skin penetrating medical device to the skin of a patient comprising the steps of puncturing the skin of the patient with a skin penetrating medical device, applying an adhesive landing zone component to the skin underneath the skin penetrating medical device, applying the landing zone component to the skin in front of the skin penetrating medical device, applying an adhesive retaining component on top of the landing zone component, and at least partially covering the skin penetrating medical device, so that an adhesive coating of the retaining component is applied to the support layer of the landing zone component.

The invention also relates to the use of a plastic film as a landing zone in application of intravenous medical devices.

DETAILED DESCRIPTION OF THE INVENTION

The fixation device of the present invention will now be described in detail together with a description of preferred embodiments with reference to the attached drawings.

As described above, there is a need for a means of fixation of skin penetrating medical devices to the skin of a patient, which are easy to apply. Skin penetrating medical devices in this context include IV penetration, such as cannulas and other needle containing devices, or drains etc.

The fixation device of the present invention is designed to securely retain a skin penetrating medical device on the skin of a patient, and comprises an adhesive landing zone component and an adhesive retaining component, which each include a support layer having an adhesive coating, and preferably a release layer to protect the adhesive coatings prior to application thereof. The landing zone component acts as a skin-contacting component and the retaining component is designed to securely affix the medical device to the patient. The retaining component may thus have a surface area which is smaller than the surface area of the landing zone component, or it may alternatively have a surface area which is equal to, or larger than, the surface area of the landing zone component.

By means of this dual component fixation device, the landing zone component can be designed to be skin-friendly, easy to apply and easy to remove from the skin, without causing discomfort to the patient, whereas the retaining component can be designed to securely affix the medical device, without consideration of skin-friendliness. The landing zone component advantageously comprises an opening, through which the skin penetrating medical device can pass when applied to the skin of a patient, thus facilitating the application of thereof to the skin.

The skin penetrating medical device may comprise a skin penetrating element, which may be a needle or a soft tubing, and a body. Whenever, the term "needle" is used hereinafter, it is intended to include any kind of skin penetrating element.

In the following description of the invention certain elements are referred to as being rear or front elements, which refers to the extension of the skin penetrating medical device which is to be fixated by means of the fixation device of the present invention. The front end of the medical device is the end where the needle is, and the rear end is where the body of the medical device is. Accordingly, front elements are to be placed at the needle end of the medical device, whereas rear elements are to be placed at the body end of the medical device.

The landing zone component, which acts as a skin-contacting component, can be applied to the skin prior to puncturing the skin with the medical device, or is advantageously applied subsequent to the operation of puncturing of the skin. When the landing zone component is applied subsequent to the action of puncturing, it is preferably inserted between the medical device and the skin of the patient, while the needle of the medical device is inserted into the patient. The release sheet is thereafter successively removed and the adhesive coating adheres to the skin behind the point of penetration. Next, a portion of the landing zone component is applied to the skin in front of the medical device. After having performed the puncturing action, the landing zone component is thus already applied to the skin of the patient, and the retaining component can easily be applied on top of the landing zone component. A portion of the landing zone component will thus be applied to the skin in the area underneath the rear part of the medical device. Thereby, the medical device is prevented from coming into direct contact with the skin of the patient, and the landing zone material has a padding function and also serves to protect the skin against scraping, thereby largely decreasing the risk for imprints and skin irritation.

By arranging a fastening means for attaching the landing zone component to the underside of the medical device, the application of the landing zone component can be essentially facilitated, since the landing zone component will be conveniently at hand already prior to initiating the puncturing operation, and will be in position to be applied to the skin, directly after puncturing. Thus, the nurse may puncture the patient and can continue to hold the medical device with one hand and remove the release layer from the landing zone component with the other hand, and press it onto the skin. As the medical device is now steadied by the landing zone component, the nurse can temporarily let go of the medical device and easily apply the retaining component on top of the landing component. The fastening means may be a double-stick tape or a pressure-sensitive adhesive, in order to allow easy fastening of the landing zone component to the medical device. In case the medical device comprises protruding elements, such as wings, the fastening means are preferably provided on the landing zone component in such a way that they will be located more or less directly below the wings of the medical device, when applied to the patient, thereby achieving a very stable fixation of the medical device. The fastening means could include a foam layer which functions as a padding in order to further enhance the protection of the skin in the area below the rear end of the medical device. The fastening means can take the form of fasteners.

The landing zone component is thus adapted to be adhesively attached to the skin around the point of penetration, i.e. where the needle of the medical device will puncture the skin. It is important that the adhesives used for the components of the fixation device are strong enough to securely fixate the medical device to the skin. The adhesive coating of both the landing zone component and the retaining component could comprise acrylic adhesive. However, the adhesive coatings of the retaining component and the landing zone component preferably comprise adhesives of different types. There is a desire to avoid aggressive and harsh adhesives in adhesive products which are to be applied directly to the skin. Therefore, the adhesive coating of the landing zone component preferably comprises a skin-friendly soft adhesive. However, in retaining an object such as a cannula, a skin-friendly soft adhesive may not be strong enough to securely hold the cannula, but a more aggressive adhesive may be required. The dual component fixation device of the present invention allows the retaining component of the present fixation device to be applied on top of the landing zone component, and thus a more aggressive adhesive can be used thereon, without causing trouble for the patient, and it also provides for a very strong fixation of the medical device. The landing zone component preferably has a surface area that is larger than the surface area of the adhesive coating of the retaining component, such that the entire surface area of the adhesive coating of the retaining component can be applied to the support layer of the landing zone component. Thereby, contact between the adhesive coating of the retaining component and the skin of the patient can be avoided.

A medical device, such as a cannula, which is attached to the skin by means of an adhesive component, will exert tearing forces and shearing forces. The retaining component therefore needs to have an adhesive coating that can withstand such forces.

Skin-friendly soft adhesives are very gentle on the skin and, when removed, basically only take dead skin cells with them. A reason for the skin-friendly properties of soft adhesives is that the adhesive does not adhere so hard to the skin, while the softness of the adhesive layer means that the adhesive, in contrast to hard adhesives, has a very good ability to follow the irregularities of the skin. This means that the contact surface area for the adhesive layer is much greater than for hard adhesives, which in turn means that it is still possible to achieve a sufficiently high overall adherence of a medical-technical article to the skin. The low adherence of soft adhesives to skin cells means that they can be removed from the skin without to any appreciable extent removing healthy skin cells with them. They can thus be removed without causing the user pain, and the absence of skin cells on a removed dressing provided with a layer of soft adhesive means that such a dressing can be reapplied with essentially the same adherence capacity.

Soft, skin-friendly adhesives can follow the contours of the skin extremely well, which means that not only is a large surface area of contact obtained by comparison with hard adhesives, but also an underpressure effect that increases the adherence of the dressing to the skin. This effect is achieved upon application by virtue of the fact that all the air under the contact surface can be pressed out when an article provided with such an adhesive coating is applied to the skin. The contact surface can be likened to mechanical suction plugs that are based entirely on the principle of creating an underpressure during loading. This effect is best ensured if the adhesive coating is of such a type that it also provides a seal against so-called microleakage, i.e. prevents air from penetrating under the contact surface between adhesive and skin, through folds or cracks in the skin. A soft silicone gel adhesive may be suitable for this purpose. Thus, the landing zone component can excellently withstand lifting forces, but is very easy to peel off.

As indicated above, the retaining component preferably has a surface area of the adhesive coating which is smaller than the surface area of the landing zone component. When the retaining component is applied so as to fix the medical device against the surface of the landing zone component the load exerted by the medical device will be concentrated to a central area of the landing zone component surface. Thereby, the forces caused by movement of the medical device on the adhesive layer of the landing zone component will rather have a lifting character, than a peeling character. This has the result that tearing forces and shearing forces at the edges of the landing zone component are rather small. The load from the medical device may lift central parts of the landing zone component from the skin, but, since very little air penetrates via the edges, the underpressure created will again suck these central parts against the skin as soon as the load ceases. Since the soft, skin-friendly adhesive does not pull off skin cells with it when the central parts lift from the skin, the component will have to a large extent the same high degree of adherence to the skin, after having been sucked firmly by the underpressure, as it does after a first application. The distance from the edges of the adhesive coating of the retaining component to the edges of the landing zone component should preferably be at least 5 mm, more preferably at least 10 mm, most preferably 15 mm or more.

The support layer of the landing zone component should preferably be flexible enough to prevent transmission of a central load directly to the edges of the component, so as to ensure that the forces are instead introduced into and distributed within the underlying adhesive layer. In this way, the forces are concentrated on the central part of the adhesive coating and decrease in the direction towards the edges, which considerably reduces the risk of the landing zone component coming loose. The landing zone support layer should therefore preferably be flexible, stretchable and also advantageously elastic, such that it recovers its original configuration after stretching. These properties also mean that the entire landing zone component can follow the irregularities of the skin and thus prevent air pockets from forming between adhesive and skin after application of the component. The landing zone support layer can be a plastic film, e.g. a polyurethane film with a thickness of 10-50 micrometers. Other plastic materials that can be used are polyester and polyethylene. The thickness of the plastic film is preferably less than 50 micrometers, more preferably 10-30 micrometers.

Advantageously, the support layer of the retaining component comprises a polyurethane film having an adhesive coating comprising an acrylic adhesive, as such adhesive is strong enough to hold a medical device in place, and can withstand tearing forces and shearing forces that are exerted by the medical device when the patient is moving.

The adhesive coating of the landing zone component preferably comprises a skin-friendly soft adhesive, such as silicone gel adhesive or soft hot-melt adhesive. Thereby, it can be ensured that adhesive coating of the landing zone will not irritate or otherwise harm the patient's skin. This is particularly advantageous for patients having fragile or sensitive skin, or who need to have long term fixation of a medical device to the skin. Soft, skin-friendly adhesives suitable for use as the adhesive coating of the landing zone component can be composed, for example, of an addition-cured RTV (Room Temperature Vulcanizing) silicone system which, after admixture, crosslinks and forms a self-adhesive gel. Examples of RTV addition-cured silicone systems are given in EP 0 300 620 A1 which describes gel-forming compositions composed of an alkenyl-substituted polydiorganosiloxane, an organosiloxane containing hydrogen atoms linked to some of the silicone atoms, and also a platinum catalyst. Wacker SilGel 612 is a commercially available RTV silicone system. This is a two-component system. The softness and degree of adherence of the gel which is formed can be varied by varying the proportions of the two components A:B from 1.0:0.7 to 1.0:1.3. Examples of other soft silicone gels that adhere to dry skin are NuSil MED-6340, NuSil MED3-6300 and NuSil MED 12-6300 from NuSil Technology, Carpintieria, Ga., USA, and Dow Corning 7-9800 from Dow Corning Corporation, Midland, USA. Other soft skin-friendly adhesives can also be used with the present invention, for example thermal adhesives such as Dispomelt® 70-4647 from National Starch and Chemical Company, Bridgewater, N.J., USA.

As indicated above the landing zone component preferably comprises an opening, through which the skin penetrating medical device can pass when applied to the skin of a patient. This may be realised by providing a landing zone component which comprises rear and front portions, which are separate from each other, so that the rear portion is adapted to be applied to the skin in the area between the skin penetrating medical device and the skin, behind the point of penetration, and the front portion is adapted to be applied to the skin, in front of the point of penetration. The medical device can thus pass through the dividing line between these two landing zone component portions. A fastening means may be arranged on the rear portion of the landing zone component to facilitate application thereof to the skin, as described above. The rear portion is then attached to the skin penetrating medical device prior to puncturing, and is subsequently applied to the skin. Thereafter, the front section is applied to the skin. The rear portion will steady the medical device during application of the front portion, and the retaining component is then applied on top of the landing zone component to fix the medical device securely. Advantageously, a cut out is provided in one or both of the rear and front portions in the side thereof, which is to be closest to the point of penetration. The cut out(s) will facilitate the forming of an opening through which the skin penetrating medical device can pass when applied to the skin of a patient, and the front and rear portions of the landing zone component are then to be applied in an overlapping or abutting fashion at the area where they meet. Alternatively, the landing zone component may be divided into portions in a different way. It may for example comprise a right hand section and a left hand section on each side of the point of penetration, or may be divided in any other way as long as the dividing line leads across the point of penetration.

The landing zone component may alternatively be in one piece, and be designed such that a front section thereof is divided into two tabs, along a dividing line leading from one end of the landing zone component to a point where the skin penetrating medical device is intended to pass through the landing zone component. If desired, an opening can be provided at the end of the dividing line where the medical device is intended to pass. When applying the landing zone component the tabs may be folded back over the rear section, to give the nurse a better view of the point of penetration. Releasable fastening means may be arranged on the rear section of the landing zone component to hold the tabs during puncturing and application of the rear portion to the skin. After having applied the rear portion to the skin, the tabs are released from the releasable fastening means and applied to the skin in front of the medical device, after having removed any release layer from the tabs. Finally, the retaining component is applied on top of the landing zone component.

Cannulas and other skin penetrating medical devices often comprise protruding elements, such as wings, which extend on each side of the medical device to improve the fixation possibilities. The retaining component, which is adapted to fix the medical device onto the surface of the landing zone component preferably comprises tabs for securing protruding elements, of the skin penetrating medical device to the landing zone component. The retaining component may include a front section from which two tabs extend in the rear direction, thus forming a rear section. The length of the tabs should be enough to reach from a point in front of the point of penetration to a point beyond the wings of the medical device.

The retaining component may be a separate component, which is adapted to be applied on top of the landing zone component.

Alternatively, the retaining component may be pre-attached to the front portion of the landing zone component, such that the front section of the retaining component is fixed to the front portion of the landing zone component, e.g. by adhesive or by welding, and the rear section of the retaining component is folded back over the front section of the retaining component, and is advantageously attached thereon by releasable fastening means. The provision of the retaining component in this way facilitates the application of the fixation device even further, as the retaining component will be conveniently at hand for attachment to the landing zone component directly subsequent to the attachment of the front portion of the landing zone component. After having applied the front portion of the landing zone component to the skin, the nurse can thus easily remove the release layer from the retaining component, release it from the fastening means and fold it over the medical device.

Figure 1:
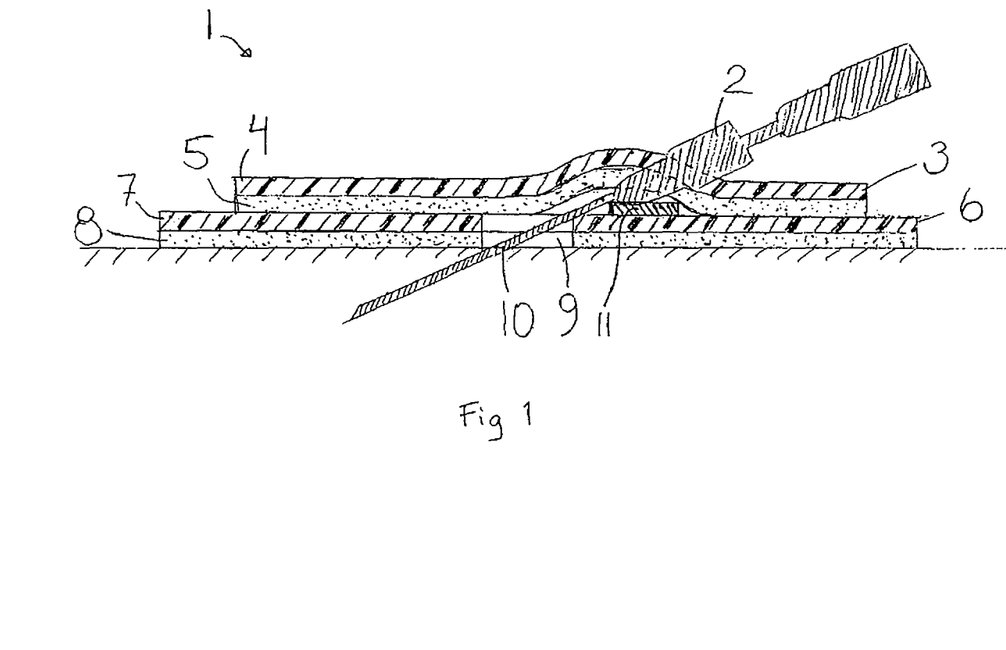
FIG. 1 shows a cross-sectional view of the fixation device when applied to the skin.

An example of the fixation device according to the invention is illustrated in FIG. 1, which shows a cross-sectional view of the fixation device 1, when applied to the skin. A landing zone component 6, comprising a support layer 7 having an adhesive coating 8, is applied to the skin of a patient. The landing zone component 6 has an opening 9 in the area of the point of penetration 10, so that the skin penetrating means of a medical device 2 (a cannula) can pass through the opening 9. A fastening means 11, e.g. in the form of a double-stick adhesive tape or a pressure sensitive adhesive is arranged on the surface of the support layer 7, such that the landing zone component is attached to the cannula by means of the fastening means 11. A retaining component 3, comprising a support layer 4 and an adhesive coating 5, is applied on top of the landing zone component 6, such that it fixes the medical device to the surface of the landing zone component.

Figure 2:
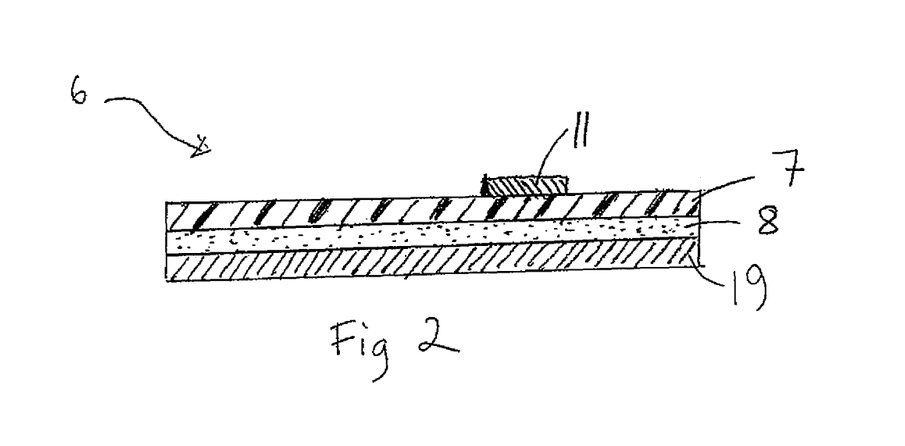
FIG. 2 shows a cross-sectional view of the landing zone component of the fixation device.
Figure 4:
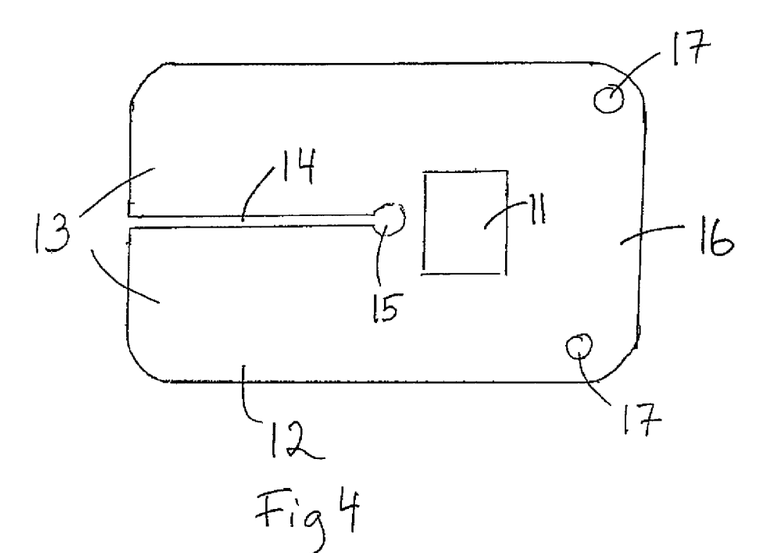
FIG. 4 shows a top view of another embodiment of the landing zone component of the fixation device.

FIG. 2 shows a cross-section of the landing zone component, including the support layer 7, adhesive coating 8, release sheet 19, fastening means 11 for attaching the landing zone component 6 to the medical device 2, and optional releasable fastening means for holding tabs of the landing zone component, cf. FIG. 4.

Figure 3:
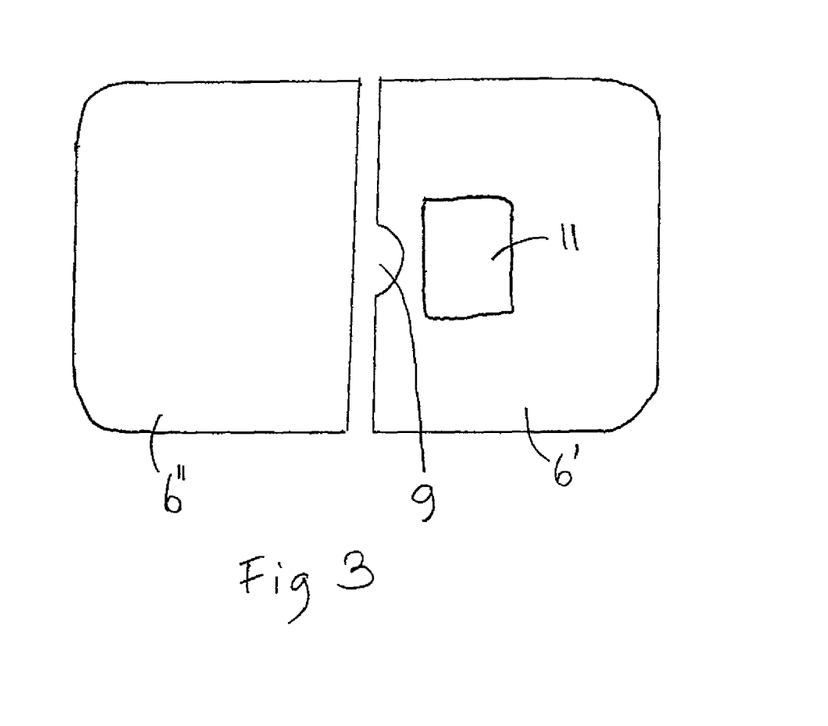
FIG. 3 shows a top view of one embodiment of the landing zone component of the fixation device.

One embodiment of the landing zone component of the fixation device is shown in FIG. 3, wherein the landing zone component comprises a rear portion 6' and a front portion 6". The rear portion 6' comprises an opening 9, in the form of a cut out, and a fastening means 11. The rear portion is intended to be attached to the medical device so that it will be placed between the medical device and the skin of the patient. The front portion is to be applied to the skin so as to abut or slightly overlap the rear portion.

FIG. 4 shows another embodiment of the landing zone component of the fixation device. In this embodiment the front section 12 of the landing zone component comprises two tabs 13, which are separated by the dividing line 14, e.g. an incision. An opening 15 may be provided at the end of the dividing line 14. Releasable fastening means 17 for holding the tabs 13 are provided on the rear section 16. By means of the releasable fastening means 17, the tabs 13 can be held in a folded back position over the rear section 16 of the landing zone component.

Figure 5:
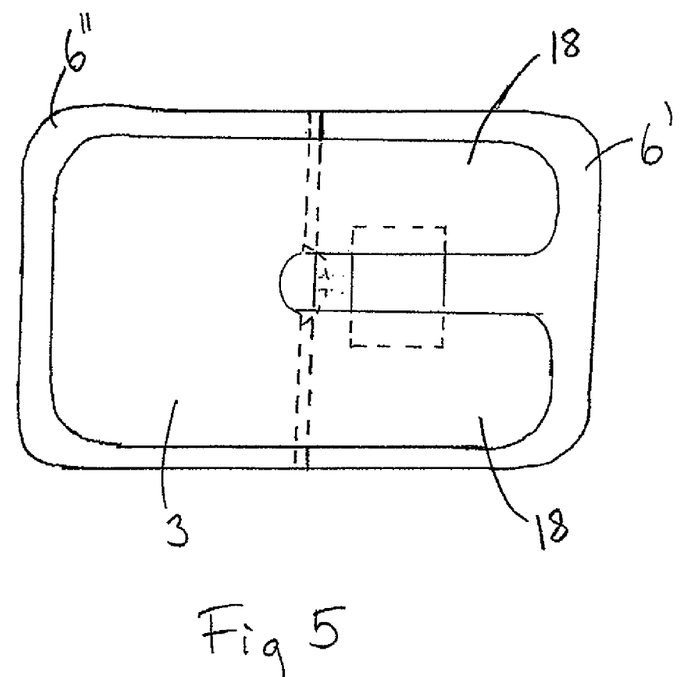
FIG. 5 shows a top view of the embodiment of the landing zone component shown in FIG. 3, having a retaining component applied thereon.

FIG. 5 shows a top view of a fixation device including a landing zone component according to the embodiment shown in FIG. 3, and a retaining component 3 applied thereon. The tabs 18 of the retaining component extend in a rearward direction, such that they can be applied over the wings of a cannula (not shown in FIG. 5).

Figure 6:
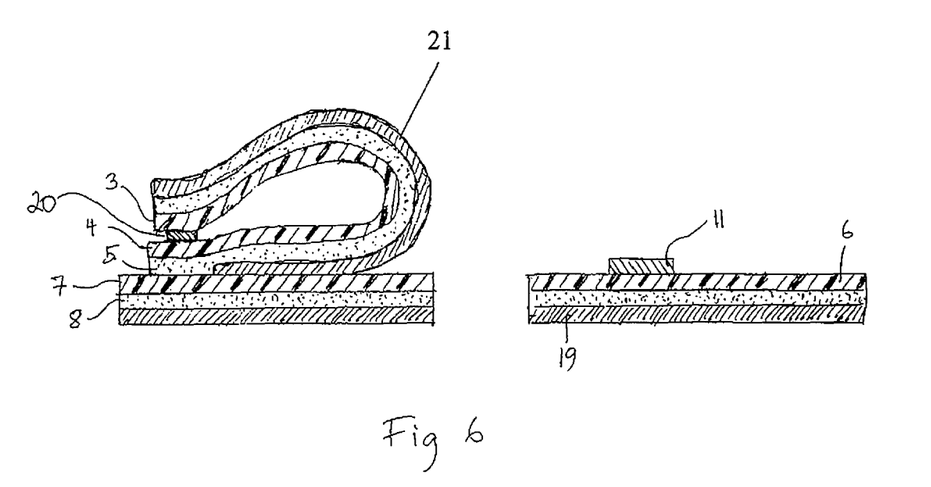
FIG. 6 shows a cross-sectional view of an alternative embodiment of the fixation device.

FIG. 6 shows a fixation device including a landing zone component according to the embodiment shown in FIG. 3, before application to a patient. The landing zone component comprises a support layer 7, an adhesive coating 8, and a release layer 19. A retaining component 3 is applied to the front portion of the landing zone component, and is folded back over its front section and releasably attached thereto by fastening means 20. The retaining component 3 includes a support layer 4, an adhesive coating 5, and a release layer 21.

The present invention also relates to a method of affixing a skin penetrating medical device 2 to the skin of a patient. The method comprises the steps of
  puncturing the skin of the patient with a skin penetrating medical device 2;
  applying an adhesive landing zone component 6 to the skin of the patient, said landing zone component 6 comprising a support layer 7 and an adhesive coating 8; and
  applying an adhesive retaining component 3 on top of the landing zone component 6, and partially covering the skin penetrating medical device 2, so that an adhesive coating 5 of the retaining component 3 is applied to the support layer 7 of the landing zone component 6;
wherein the step of applying the adhesive landing zone component 6 includes applying the adhesive landing zone component 6 to the skin underneath the skin penetrating medical device 2, and applying the landing zone component to the skin in front of the skin penetrating medical device 2; and wherein the step of applying the landing zone component can be performed prior to or subsequent to puncturing the skin with the skin penetrating medical device 2.

The landing zone component 6 may be attached to the skin penetrating medical device 2 prior to puncturing of the skin, so as to allow easy application thereof. When the landing zone component comprises a rear portion 6' and a front portion 6", the rear portion 6' is preferably applied to the skin prior to applying the front portion 6".

If desired, the rear portion 6' may be applied to the skin prior to puncturing of the skin, and the front portion 6" be applied to the skin subsequent to puncturing of the skin.

The invention also relates to the use of a plastic film as a landing zone component in application of an intravenous medical device, said landing zone being adapted to receive a retaining component for holding a medical device, and said plastic film having a thickness of 10-50 micrometers, and being provided with an adhesive coating. The plastic film and the adhesive coating may be chosen among any of the materials described above in connection with the landing zone component of the fixation device. A soft skin-friendly adhesive, in particular a silicone gel adhesive or soft hot-melt adhesive, is preferred.

The described embodiments of the invention can of course be modified within the scope of the invention. For example, the landing zone component and the retaining component could have other shapes that those illustrated in the drawings, and the retaining device can be modified so as to allow retaining of the skin penetrating medical devices of various types. The invention is thus limited only scope of the attached patent claims.

The invention claimed is:

1. A fixation device for retaining a skin penetrating medical device on the skin of a patient, said fixation device comprising:
   a retaining component, including a support layer having a first adhesive coating; and
   a landing zone component, including a support layer having a second adhesive coating, said landing zone component acting as a skin-contacting component and being adapted to be adhesively attached to the skin around a point of penetration of the skin penetrating medical device, wherein said landing zone component has a surface area that is larger than the surface area of the first adhesive coating of the retaining component,
   wherein said retaining component is adapted to affix the medical device, and is adapted to be applied on top of the landing zone component to concentrate a load exerted by the skin penetrating medical device to a central area of the landing zone component, and at least partially cover the skin penetrating medical device, such that the first adhesive coating of the retaining component is applied to the support layer of the landing zone component, and wherein the first adhesive coating of the retaining component comprises a first adhesive, and the second adhesive coating of the landing zone component comprises a second adhesive, said first adhesive being different from said second adhesive, wherein the first adhesive of the retaining component comprises an acrylic adhesive, and the second adhesive of the landing zone component comprises a soft, skin-friendly adhesive comprising a silicone gel adhesive or soft hot-melt adhesive.

2. The fixation device of claim 1, wherein a first fastener is provided for attaching the landing zone component to the skin penetrating medical device.

3. The fixation device of claim 2, wherein the first fastener is a double-stick tape or a pressure-sensitive adhesive.

4. The fixation device of claim 1, wherein the landing zone component has an opening, through which the skin penetrating medical device can pass when applied to the skin of a patient.

5. The fixation device of claim 1, wherein the landing zone component comprises a rear portion, and a front portion, said rear and front portions being separate from each other, and said rear portion being adapted to be applied to the skin in the area between the skin penetrating medical device and the skin, behind the point of penetration, and said front portion being adapted to be applied to the skin, in front of the point of penetration.

6. The fixation device of claim 5, wherein at least one of the rear and front portions has a cut out in a side thereof, which is to be closest to the point of penetration, said cut out forming an opening through which the skin penetrating medical device can pass when applied to the skin of a patient.

7. The fixation device of claim 1, wherein a front section of the landing zone component is divided into two tabs, along a dividing line leading from one end of the landing zone component to a point where the skin penetrating medical device is intended to pass through the landing zone component.

8. The fixation device of claim 7, wherein a rear section of the landing zone component comprises a second fastener for holding the tabs in a position in which they are folded back over the rear section.

9. The fixation device of claim 1, wherein the retaining component comprises tabs for securing protruding elements of the skin penetrating medical device to the landing zone component.

10. The fixation device of claim 9, wherein the protruding elements comprise wings.

11. The fixation device of claim 1, wherein the distance from the edges of the first adhesive coating of the retaining component to the edges of the landing zone component is at least 5 mm.

12. The fixation device of claim 1, wherein the distance from the edges of the first adhesive coating of the retaining component to the edges of the landing zone component is at least 15 mm.

13. A landing zone component for use in a fixation device for retaining a skin penetrating medical device on the skin of a patient, said landing zone component acting as a skin-contacting component and comprising:
   a support layer having an adhesive coating, wherein said landing zone component has an opening, through which the skin penetrating medical device can pass when the landing zone component is applied to the skin of a patient, and wherein the adhesive coating comprises a soft, skin-friendly adhesive comprising a silicone gel adhesive or soft hot-melt adhesive; and
   a third fastener for attaching the landing zone component to the skin penetrating medical device, wherein the third fastener is configured on the support layer to concentrate a load exerted by the skin penetrating medical device to a central area of the landing zone component.

14. The landing zone component of claim 13, wherein the third fastener is a double-stick tape or a pressure-sensitive adhesive.

15. The landing zone component of claim 13, further comprising a rear portion, and a front portion, said rear portion being adapted to be applied to the skin in the area between the skin penetrating medical device and the skin, behind a point of penetration where the medical device enters the skin, and said front portion being adapted to be applied to the skin in front of the point of penetration.

16. The landing zone component of claim 15, wherein at least one of the rear and front portions has a cut out in a side thereof, which is to be closest to the point of penetration, said cut out forming an opening through which the skin penetrating medical device can pass when applied to the skin of a patient.

17. The landing zone component of claim 13, wherein a front section of the landing zone component is divided into two tabs, along a dividing line leading from one end of the landing zone component to a point where the skin penetrating medical device is intended to pass through the landing zone component.

18. The landing zone component of claim 17, wherein a rear section of the landing zone component comprises a fourth fastener for holding the tabs in a position in which they are folded back over the rear section.

19. A method of affixing a skin penetrating medical device to the skin of a patient comprising the steps of:
   puncturing the skin of the patient with the skin penetrating medical device;
   applying an adhesive landing zone component to the skin of the patient, said landing zone component comprising a support layer and an adhesive coating comprising a soft, skin-friendly adhesive comprising a silicone gel adhesive or soft hot-melt adhesive; and
   applying an adhesive retaining component on top of the landing zone component, and partially covering the skin penetrating medical device, so that an adhesive coating of the retaining component is applied to the support layer of the landing zone component to concentrate a load exerted by the skin penetrating medical device to a central area of the landing zone component, wherein the adhesive coating of the retaining component comprises an acrylic adhesive,
   wherein said landing zone component has a surface area that is larger than the surface area of the first adhesive coating of the retaining component,
   wherein the step of applying the adhesive landing zone component includes applying the adhesive landing zone component to the skin underneath the skin penetrating medical device, and applying the landing zone component to the skin in front of the skin penetrating medical device, and wherein the step of applying the landing zone component can be performed prior to or subsequent to puncturing the skin with the skin penetrating medical device.

20. The method of claim 19, wherein the landing zone component is attached to the skin penetrating medical device prior to puncturing of the skin.

21. The method of claim 19, wherein the landing zone component comprises a rear portion and a front portion, and the rear portion is applied to the skin prior to applying the front portion.

22. The method of claim 21, wherein the rear portion is applied to the skin prior to puncturing of the skin, and the front portion is applied to the skin subsequent to puncturing of the skin.

* * * * *